United States Patent
Vaillant et al.

(10) Patent No.: US 12,048,575 B2
(45) Date of Patent: Jul. 30, 2024

(54) SYSTEMS AND METHODS FOR REGISTRATION OF ANGIOGRAPHIC PROJECTIONS WITH COMPUTED TOMOGRAPHIC DATA

(71) Applicant: GE Precision Healthcare LLC, Milwaukee, WI (US)

(72) Inventors: Régis Vaillant, Villebon sur Yvette (FR); Liliane Ramus, Versailles (FR); Sophie Amelot, Marly le Roi (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 62 days.

(21) Appl. No.: 16/814,780

(22) Filed: Mar. 10, 2020

(65) Prior Publication Data

US 2021/0282731 A1 Sep. 16, 2021

(51) Int. Cl.
*A61B 6/50* (2024.01)
*A61B 6/00* (2024.01)
*A61B 6/03* (2006.01)
*A61B 6/46* (2024.01)

(52) U.S. Cl.
CPC ............ *A61B 6/504* (2013.01); *A61B 6/035* (2013.01); *A61B 6/466* (2013.01); *A61B 6/503* (2013.01); *A61B 6/5217* (2013.01)

(58) Field of Classification Search
CPC ....... A61B 6/504; A61B 6/035; A61B 6/5217; A61B 6/466; A61B 6/503; A61B 6/5229
See application file for complete search history.

(56) References Cited

U.S. PATENT DOCUMENTS

| | | | |
|---|---|---|---|
| 8,948,487 B2 | 2/2015 | Sundar | |
| 9,375,191 B2* | 6/2016 | Verstraelen | ........... A61B 6/469 |
| 9,785,746 B2 | 10/2017 | Fonte et al. | |
| 9,858,387 B2 | 1/2018 | Lavi et al. | |
| 9,891,044 B2 | 2/2018 | Tu et al. | |
| 2006/0274928 A1* | 12/2006 | Collins | ................. G16H 30/40 |
| | | | 382/132 |

(Continued)

FOREIGN PATENT DOCUMENTS

WO 2018178272 A1 10/2018

OTHER PUBLICATIONS

Georgoulia, P. et al. "Myocardial Perfusion (SPECT) Imaging: Radiotracers and Techniques". Frontiers in Heart Failure, 2016, vol. 2, 68-123 (Year: 2016).*

(Continued)

*Primary Examiner* — Keith M Raymond
*Assistant Examiner* — Milton Truong
(74) *Attorney, Agent, or Firm* — McCoy Russell LLP (57) ABSTRACT

Systems and methods are provided for imaging coronary trees via registration of angiographic projections with computed tomographic data. In one example, a method for imaging a coronary artery of interest in a patient may include acquiring computed tomography (CT) imaging data depicting a coronary tree, acquiring a single angiographic projection of the coronary artery of interest, registering the single angiographic projection to the CT imaging data, and determining a fractional flow reserve (FFR) of the coronary artery of interest based on the single angiographic projection registered to the CT imaging data.

16 Claims, 4 Drawing Sheets

(56) References Cited

U.S. PATENT DOCUMENTS

| | | | |
|---|---|---|---|
| 2010/0014740 A1* | 1/2010 | Movassaghi | A61B 6/504 382/132 |
| 2014/0200867 A1* | 7/2014 | Lavi | G16H 30/20 703/2 |
| 2014/0249790 A1* | 9/2014 | Spilker | G06T 7/0012 703/11 |
| 2014/0313196 A1* | 10/2014 | Mistretta | A61B 6/504 345/424 |
| 2015/0262357 A1* | 9/2015 | Igarashi | A61B 6/463 382/131 |
| 2017/0076046 A1* | 3/2017 | Barnes | G06Q 10/06 |
| 2018/0032653 A1 | 2/2018 | Aben et al. | |
| 2018/0061047 A1 | 3/2018 | Redel | |
| 2018/0211729 A1 | 7/2018 | Grass | |
| 2018/0330484 A1* | 11/2018 | Bauer | A61B 6/504 |
| 2019/0122769 A1* | 4/2019 | Wright | G06F 3/0482 |
| 2020/0029917 A1* | 1/2020 | Kudo | A61B 6/4078 |
| 2020/0118264 A1* | 4/2020 | Harish | A61B 6/504 |
| 2020/0155103 A1* | 5/2020 | Mistretta | A61B 5/0285 |
| 2020/0222018 A1* | 7/2020 | van Walsum | A61B 6/464 |

OTHER PUBLICATIONS

Pijls, N. et al., "Percutaneous Coronary Intervention of Functionally Nonsignificant Stenosis," Journal of the American College of Cardiology, vol. 49, No. 21, May 29, 2007, 7 pages.

Tonino, P. et al., "Fractional Flow Reserve versus Angiography for Guiding Percutaneous Coronary Intervention," The New England Journal of Medicine, vol. 360, No. 3, Jan. 15, 2009, 11 pages.

Benseghir, T. et al., "A tree-topology preserving pairing for 3D/2D registration," International Journal of Computer Assisted Radiology and Surgery, vol. 10, No. 6, Jun. 2015, 11 pages.

Neumann, F. et al., "2018 ESC/EACTS Guidelines on myocardial revascularization," European Heart Journal, vol. 40, No. 2, Aug. 25, 2018, 7 pages.

Poulain, E. et al., "3D Coronary Vessel Tree Tracking in X-Ray Projections," Proceedings of the 10th International Conference on Functional Imaging of the Heart, Functional Imaging and Modeling of the Heart (FIMH 2019), Jun. 8, 2019, Bordeaux, France, 9 pages.

EP application 21159099.7 filed Feb. 24, 2021—Search Report issued Oct. 21, 2021; 14 pages.

Snidow J J et al: "Three-Dimensional Gadolinium-Enhanced MR Angiography for Aortoiliac Inflow Assessment Plus Renal Artery Screening in a Single Breath Hold", Radiology, Radiological Society of North America, Inc, US, vol. 198, No. 3, Mar. 1, 1996 (Mar. 1, 1996), pp. 725-732, XP008031577, ISSN: 0033-8419.

JP application 2021-035870 filed Mar. 5, 2021—Office Action issued Apr. 20, 2022, Machine Translation, 4 pages.

CN application 202110218607.7 filed Feb. 26, 2021—Office Action issued Mar. 14, 2024, 12 pages.

* cited by examiner

//SYSTEMS AND METHODS FOR REGISTRATION OF ANGIOGRAPHIC PROJECTIONS WITH COMPUTED TOMOGRAPHIC DATA

FIELD

Embodiments of the subject matter disclosed herein relate to medical imaging, and more particularly to registration of images obtained via invasive angiographic techniques with computed tomographic data.

BACKGROUND

Invasive angiographic procedures may involve the insertion and threading of a catheter into an artery, via which a contrast dye may be injected. X-rays attenuated by the artery filled with the contrast dye may then be acquired via x-ray imaging techniques, thereby generating a high-resolution, two-dimensional (2D) projection of a region of the coronary tree. In some examples, multiple 2D projections may be employed to obtain an accurate three-dimensional (3D) and functional representation of the coronary tree by manual or automatic registration of the 2D projections with one another.

Computed tomography (CT) angiography is an alternative, non-invasive technique for diagnosing coronary ailments. Specifically, in CT angiography, the contrast dye may instead be provided via intravenous injection (e.g., via a needle). As such, patient discomfort may be significantly decreased as compared to invasive angiography. Further, CT angiography may be employed to image an entirety of the coronary tree. However, images obtained from CT angiography may have lower resolution in specific situations, such as when a patient has a stenosis or a high heart rate.

BRIEF DESCRIPTION

In one embodiment, a method for imaging a coronary artery of interest in a patient may include acquiring computed tomography (CT) imaging data depicting a coronary tree, acquiring a single angiographic projection of the coronary artery of interest, registering the single angiographic projection to the CT imaging data, and determining a fractional flow reserve (FFR) of the coronary artery of interest based on the single angiographic projection registered to the CT imaging data.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
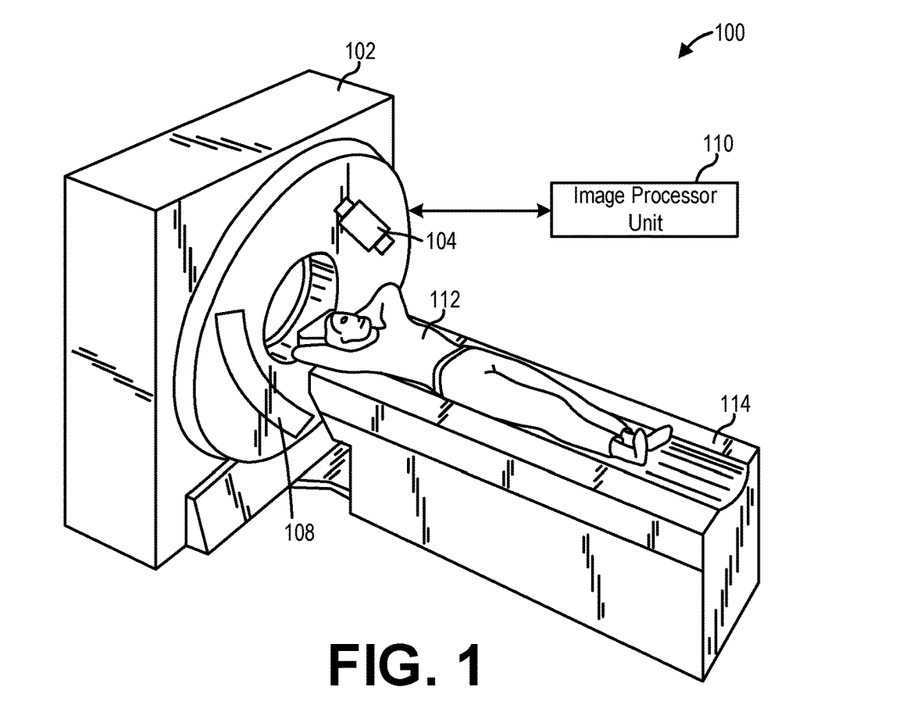
FIG. 1 shows a pictorial view of an exemplary medical imaging system, according to an embodiment.
Figure 2:
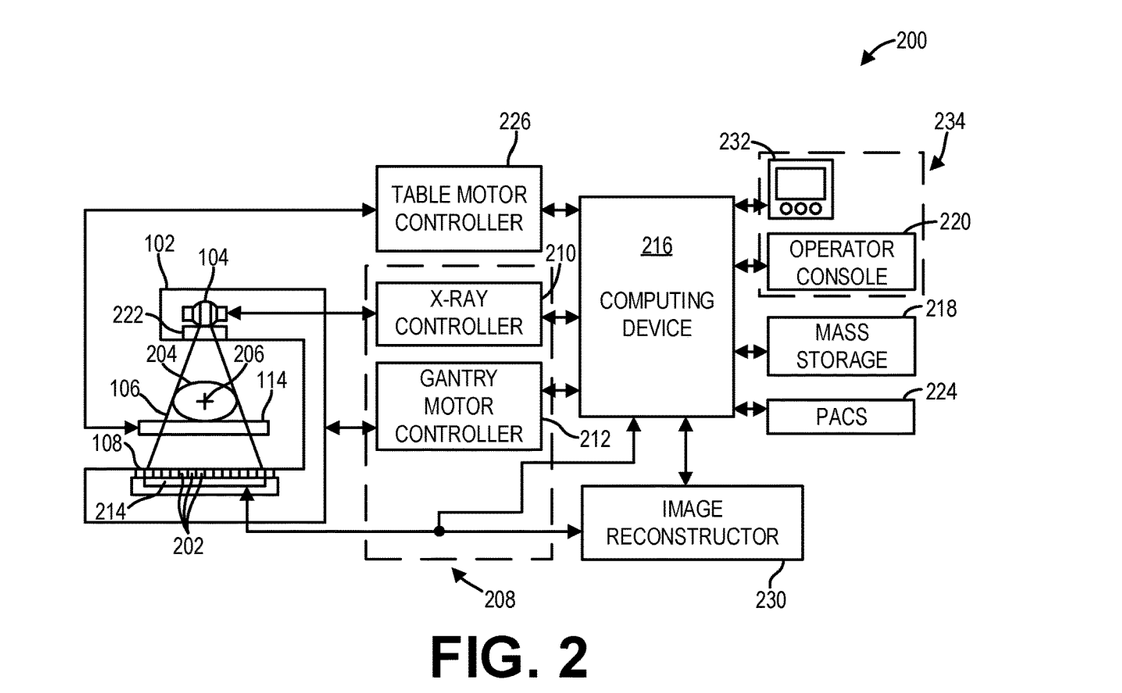
FIG. 2 shows a schematic block diagram of the exemplary medical imaging system, according to an embodiment.

The following description relates to various embodiments of medical imaging systems, and of methods for automatically registering two-dimensional (2D) angiographic projections to three-dimensional (3D) computed tomographic (CT) imaging data thereon. One such medical imaging system configured to acquire the 2D angiographic projections and the 3D CT imaging data is depicted in FIGS. 1 and 2, and one such method for automatically registering the 2D angiographic projections to the 3D CT imaging data is provided in FIGS. 3A and 3B, from which a fractional flow reserve (FFR) of a coronary artery of interest may be determined. In one embodiment, the FFR may be estimated by forming a reduced order model based on the 2D angiographic projections automatically registered to the 3D CT imaging data, such as the exemplary reduced order model of FIG. 4. FIG. 5 depicts an exemplary user interface display of a display device of the medical imaging system, where a reconstructed image based on the 2D angiographic projections registered to the 3D CT imaging data, the FFR of the coronary artery of interest, and a diagnosis and a recommended treatment based on the FFR are displayed simultaneously.

In general, the FFR is a physiological index which may be used, for example, to determine a hemodynamic severity of intracoronary lesions or to identify a lesion responsible for ischemia. As such, the FFR may serve as an indicator of therapeutic strategies for treating a coronary artery of interest in a given patient. For example, relatively smaller FFRs may indicate selection of a revascularization technique (e.g., angioplasty) as treatment for a correspondingly constricted coronary artery, whereas relatively larger FFRs may indicate selection of another medical treatment (e.g., prescription medication) as treatment.

Specifically, the FFR is a ratio of an arterial pressure distal to (e.g., upstream of) a lesion to an arterial pressure proximal to (e.g., downstream of) the lesion. As an example, the arterial pressure proximal to the lesion may be taken at an ostia of the coronary tree, and may therefore be considered as the aortic pressure at hyperemia. In some cases, the arterial pressure distal to the lesion may be measured invasively, e.g., via a pressure sensor placed distal to the lesion. However, from a patient workflow perspective, less invasive methods may be desired (e.g., to mitigate patient discomfort).

In some examples, the FFR may be determined via CT angiographic imaging alone. Once CT angiographic imaging data is received, vessel centerlines and vessel edges may be segmented to determine lengths and three-dimensional shapes of the coronary arteries. Such segmentation methods remain formidable challenges in the art, requiring top quality imaging for accurate diagnosis. Further, automatically processing imaged vessel lumen may be difficult in patients with calcified vessels (e.g., stenosis) or high heart rates. As such, medical professionals may verify the segmentation, which may result in inconsistencies in diagnosis, treatment, and health outcomes.

In other examples, the FFR may be determined via invasive angiographic imaging alone. Invasive angiographic imaging data may be received as a plurality of 2D angiographic projections which present different views of the coronary artery of interest. The plurality of 2D angiographic projections may then be registered to one another, e.g., via a stereo vision imaging algorithm, so as to obtain a 3D model of the coronary artery of interest. However, acquiring the plurality of 2D angiographic projections may be uncomfortable for the patient. Further, medical professionals often may be employed to manually mark a location of the coronary artery of interest in each of the plurality of 2D angiographic projections for inputting into the stereo vision imaging algorithm. Similar to CT angiographic imaging, such manual interaction with the imaging data may result in inconsistencies in diagnosis, treatment, and health outcomes.

Accordingly, in embodiments described herein, systems and methods are provided for automatically registering a single 2D angiographic projection to the 3D CT angiographic imaging data. As such, a 3D representation of an entire coronary tree may be obtained via CT angiographic imaging and the single 2D angiographic projection may be employed for areas of coronary arteries which may be difficult to capture in the 3D CT angiographic imaging data. In some embodiments, the FFR may then be estimated via segmentation of the resulting imaging data and forming a reduced order model therefrom. Further, in certain embodiments, the 3D CT angiographic imaging data may have been previously imaged and may thus be acquired from an imaging library, such that only the single 2D angiographic projection need be imaged. Accordingly, by combining invasive angiographic imaging data with CT angiographic imaging data in this way, patient discomfort may be mitigated and total imaging time may be decreased through minimization of imaging procedures. Additionally, the methods for automated registration provided herein may reduce the aforementioned inconsistencies in diagnosis, treatment, and health outcomes. As such, an overall patient experience may be improved.

Referring now to FIG. 1, an exemplary imaging system 100 is depicted according to an embodiment. In the illustrated embodiment, the imaging system 100 is an x-ray imaging system configured to perform angiographic imaging. In some embodiments, the angiographic imaging may include invasive angiographic imaging techniques and/or CT angiographic imaging techniques. However, it is understood that embodiments set forth herein may be implemented using other types of medical imaging modalities (e.g., x-ray, magnetic resonance (MR), ultrasound (US), positron emission tomography (PET), single-photon emission CT (SPECT), and combinations thereof, e.g., multi-modality imaging, such as PET/CT, PET/MR, SPECT/CT, etc.). Furthermore, it is understood that other embodiments do not actively acquire medical images. Instead, embodiments may retrieve images or imaging data that was previously acquired by an imaging system and analyze the imaging data as set forth herein.

The imaging system 100 may be configured to image a subject 112 such as a patient, an inanimate object, one or more manufactured parts, and/or foreign objects such as dental implants, stents, and/or contrast agents present within the body. In one embodiment, the imaging system 100 may include a gantry 102, which in turn, may further include at least one x-ray source 104 configured to project a beam of x-ray radiation 106 (see FIG. 2) for use in imaging the subject 112 laying on a table 114. Specifically, the x-ray source 104 may be configured to project the x-rays 106 towards a detector array 108 positioned on the opposite side of the gantry 102. Although FIG. 1 depicts a single x-ray source 104, in certain embodiments, multiple x-ray sources and/or detectors may be employed to project a plurality of x-ray radiation beams 106 for acquiring projection data at different energy levels or angular orientations corresponding to the subject 112. In some CT imaging embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the gantry 102 may be a C-arm gantry, configured such that the x-ray source 104 may project the beam of x-ray radiation 106 towards a predetermined target location within the subject 112. For example, in invasive angiographic imaging applications, a catheter may be inserted into the subject 112 so as to inject a contrast dye at the predetermined target location whereat the beam of x-ray radiation 106 is expected to pass through the subject 112. Accordingly, after passing through the subject 112 and being attenuated by various anatomical features and the contrast dye, the beam of x-ray radiation 106 may be received by the detector array 108 disposed opposite to the x-ray source 104.

In certain embodiments, the imaging system 100 further includes an image processor unit 110 configured to reconstruct images of a target volume of the subject 112 using an iterative or analytic image reconstruction method, or a combination of both. For example, in CT imaging applications, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR) or model-based iterative reconstruction (MBIR), and the like, to reconstruct images of a target volume of the subject 112. In some examples, the image processor unit 110 may use both an analytic image reconstruction approach such as FBP in addition to an iterative image reconstruction approach.

In some imaging system configurations (e.g., CT imaging system configurations), an x-ray source projects a cone-shaped x-ray radiation beam which is collimated to lie within an X-Y-Z plane of a Cartesian coordinate system (generally referred to as an "imaging plane"). The x-ray radiation beam passes through an object being imaged, such as the patient or subject. The x-ray radiation beam, after being attenuated by the object, impinges upon an array of radiation detectors. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some imaging systems (e.g., CT imaging systems), the x-ray source and the detector array are rotated with a gantry about the imaging plane and around the object to be imaged such that an angle at which the radiation beam intersects the object constantly changes. A group of x-ray radiation attenuation measurements, e.g., projection data, from the detector array at one angular position of the gantry is referred to as a "view." A "scan" of the object includes a set of views made at different angular positions, or view angles, during one revolution of the x-ray source and detector about the object. It is contemplated that the benefits of the methods described herein accrue to many medical imaging modalities, so as used herein the term "view" is not limited to the use as described above with respect to projection data from one gantry angle. The term "view" is used to mean one data acquisition whenever there are multiple data acquisitions from different angles, whether from a CT, x-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers (called "CT numbers" or "Hounsfield units" in the case of a CT imaging system), which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 2, an exemplary imaging system 200 similar to the imaging system 100 of FIG. 1 is depicted. That is, the imaging system 200 may be an x-ray imaging system configured for invasive angiographic imaging and/or CT angiographic imaging. As shown, the imaging system 200 may include multiple components. The components may be coupled to one another to form a single structure, may be separate but located within a common room, or may be remotely located with respect to one another. For example, one or more of the modules described herein may operate in a data server that has a distinct and remote location with respect to other components of the imaging system 200.

In accordance with aspects of the present disclosure, the imaging system 200 may be configured for imaging a subject 204 (e.g., the subject 112 of FIG. 1). In one embodiment, the imaging system 200 may include the detector array 108 (see FIG. 1). The detector array 108 may further include a plurality of detector elements 202 that together sense the x-ray radiation beams 106 that pass through the subject 204 (such as a patient) to acquire corresponding projection data. Accordingly, in one embodiment, the detector array 108 may be fabricated in a multi-slice configuration including the plurality of rows of cells or detector elements 202. In such a configuration, one or more additional rows of the detector elements 202 may be arranged in a parallel configuration for acquiring the projection data.

In certain embodiments, the imaging system 200 may be configured to include a substantially C-shaped or semicircular gantry or "C-arm" 102. The gantry 102 may movably support the x-ray source 104 and the detector array 108 mounted opposite to each other on opposed ends. The subject 204 may accordingly be disposed between the x-ray source 104 and the detector array 108, supported by the table 114.

It will be recognized that in some embodiments, the table 114 may further be movable to achieve a desired image acquisition. During such an acquisition of image data, the gantry 102 may be movable to change a position and/or orientation of the x-ray source 104 and/or the detector array 108 relative to the subject 204.

Accordingly, in some embodiments, such as in invasive angiographic imaging applications, the gantry 102 may remain fixed during a given imaging session so as to image a single 2D projection of the subject 204. In such embodiments, a position of the gantry 102 and/or the table 114 may be adjusted between imaging sessions so as to image another view of the subject 204.

In still other embodiments, such as in CT imaging applications, the imaging system 200 may be configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In such embodiments, as the x-ray source 104 and the detector array 108 rotate, the detector array 108 may collect data of the attenuated x-ray beams. The data collected by the detector array 108 may undergo preprocessing and calibration to condition and process the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections may be converted to a set of material-density projections. The material-density projections may be reconstructed to form a pair or a set of material-density maps or images of each respective basis material, such as bone, soft tissue, and/or contrast agent maps. The material-density maps or images may be, in turn, associated to form a volume rendering of the basis material, for example, bone, soft tissue, and/or contrast agent, in the imaged volume.

Once reconstructed, the basis material image produced by the imaging system 200 may reveal internal features of the subject 204, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the imaging system 200 may include a control mechanism 208 to control movement of the components such as rotation of the gantry 102 and the operation of the x-ray source 104. In certain embodiments, the control mechanism 208 may further include an x-ray controller 210 configured to provide power and timing signals to the x-ray source 104. In additional or alternative embodiments, the x-ray controller 210 may further provide operational and/or control signals to an adjustable collimator 222 to shape the x-ray beam from the x-ray source 104 in accordance with a given imaging procedure to be performed. Additionally, the control mechanism 208 may include a gantry motor controller 212 configured to control a rotational speed and/or position (rectilinear or curvilinear) of the gantry 102 or of various components thereof (e.g., the x-ray source 104, the detector array 108, etc.) based on imaging requirements.

In certain embodiments, the control mechanism 208 may further include a data acquisition system (DAS) 214 configured to sample analog data received from the detector elements 202 and convert the analog data to digital signals for subsequent processing. For photon-counting imaging systems, the DAS 214 may download measured photon counts in one or more energy bins from detector array 108. The DAS 214 may be further configured to selectively aggregate analog data from a subset of the detector elements 202 into so-called macro-detectors, as described further herein.

The data sampled and digitized by the DAS 214 may be transmitted to a computer or computing device 216. In the illustrated embodiment, the computing device 216 may be configured to interface with various components of the imaging system 200. As such, the computing device 216 may be configured to control operation of the imaging system 200. In various embodiments, the computing device 216 may take the form of a mainframe computer, server computer, desktop computer, laptop computer, tablet device, network computing device, mobile computing device, mobile communication device, etc. In one embodiment, the computing device 216 may take the form of an edge device for interfacing between the various components of FIG. 2. In some embodiments, the one or more components of the imaging system 200 configured to acquire x-ray radiation may be considered an x-ray imaging subsystem (e.g., the x-ray source 104, the detector array 108, etc.) of the overall imaging system 200, which may be a computing system further configured to interface with a user and perform a variety of computational processes (e.g., imaging or non-imaging). Accordingly, other components (e.g., the computing device 216, etc.) of the imaging system 200 may be communicably coupled to the x-ray imaging subsystem.

In some embodiments, the computing device 216 may store the data in a storage device or mass storage 218, either included in the computing device 216 (in such examples, the computing device 216 may be referred to as a controller) or a separate device communicably coupled to the computing device 216 (in such examples, the computing device 216 may be referred to as a processor). The storage device 218 may include removable media and/or built-in devices. Specifically, the storage device 218 may include one or more physical, non-transitory devices configured to hold data and/or instructions executable by the computing device 216 to implement the herein described methods. Accordingly, when such methods are implemented, a state of the storage device 218 may be transformed (for example, to hold different, or altered, data). The storage device 218, for example, may include magnetoresistive random-access memory (MRAM), a hard disk drive, a floppy disk drive, a tape drive, a compact disk-read/write (CD-R/W) drive, a Digital Versatile Disc (DVD) drive, a high-definition DVD (HD-DVD) drive, a Blu-Ray drive, a flash drive, and/or a solid-state storage drive. It will be appreciated that the storage device 218 may be a non-transitory storage medium.

Additionally, the computing device 216 may provide commands and parameters to one or more of the DAS 214, the x-ray controller 210, and the gantry motor controller 212 for controlling system operations such as data acquisition and/or processing. In certain embodiments, the computing device 216 controls system operations based on operator input, e.g., via a user interface 234. The computing device 216 receives the operator input, for example, including commands and/or scanning parameters via an operator console 220 operatively coupled to the computing device 216. The operator console 220 may include a physical keyboard, mouse, touchpad, and/or touchscreen to allow the operator to specify the commands and/or scanning parameters.

Although FIG. 2 illustrates only one operator console 220, more than one operator console 220 may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 may either include, or may be coupled to, a picture archiving and communications system (PACS) 224. In an exemplary implementation, the PACS 224 may further be coupled to a remote system such as radiological information systems (e.g., RIS), electronic health or medical records and/or hospital information systems (e.g., EHR/HIS), and/or to an internal or external network (not shown) to allow operators at different locations to supply commands and parameters and/or gain access to the image data.

The computing device 216 may use the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. For example, one embodiment may use computing resources in a "cloud" network cluster for the image reconstructor 230.

In one embodiment, the image reconstructor 230 may store the images reconstructed in the storage device 218, either via the computing device 216 as shown in FIG. 2 or via a direct connection (not shown). Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods or processes (such as the method described below with reference to FIGS. 3A and 3B) described further herein may be stored as executable instructions in non-transitory memory on a computing device (or controller), or in communication with a computing device (or processor), in the imaging system 200. In one embodiment, the image reconstructor 230 may include such executable instructions in non-transitory memory, and may apply the methods described herein to reconstruct an image from scanning data. In another embodiment, the computing device 216 may include the instructions in non-transitory memory, and may apply the methods described herein, at least in part, to a reconstructed image after receiving the reconstructed image from the image reconstructor 230. In yet another embodiment, the methods and processes described herein may be distributed across the image reconstructor 230 and the computing device 216.

In operation, the computing device 216 may acquire imaging data and other medical data, which may be translated for display to a user (e.g., a medical professional) via the user interface 234, for example, on the display device 232. As an example, the medical data may be transformed into and displayed at the display device 232 as a user-facing graphical and/or textual format, which may be standardized across all implementations of the imaging system 200 or may be particular to a given facility, department, profession, or individual user. As another example, the imaging data (e.g., three-dimensional (3D) volumetric data sets, two-dimensional (2D) imaging slices, etc.) may be used to generate one or more images at the computing device 216, which may then be displayed to the operator or user at the display device 232. As such, the display device 232 may allow the operator to evaluate the imaged anatomy. The display device 232 may also allow the operator to select a volume of interest (VOI) and/or request patient information, for example, via a graphical user interface (GUI) for a subsequent scan or processing. A specific example of a display which may be presented to the user via the display device 232 is provided hereinbelow with reference to FIG. 5.

It will be appreciated that the imaging systems described above with reference to FIGS. 1 and 2 may be configured for CT angiographic imaging, invasive angiographic imaging, another imaging modality, or combinations thereof. Thus, in some embodiments, multiple gantries 102 each having respective x-ray sources 104, detector arrays 108, etc. may be provided for differing imaging applications. In other embodiments, a separate imaging system may be provided for each of a plurality of imaging modalities, where the separate imaging systems may be communicatively coupled via a wired or wireless network. In such embodiments, imaging data may transmitted and received between the separate imaging systems via the network.

Figure 3A:
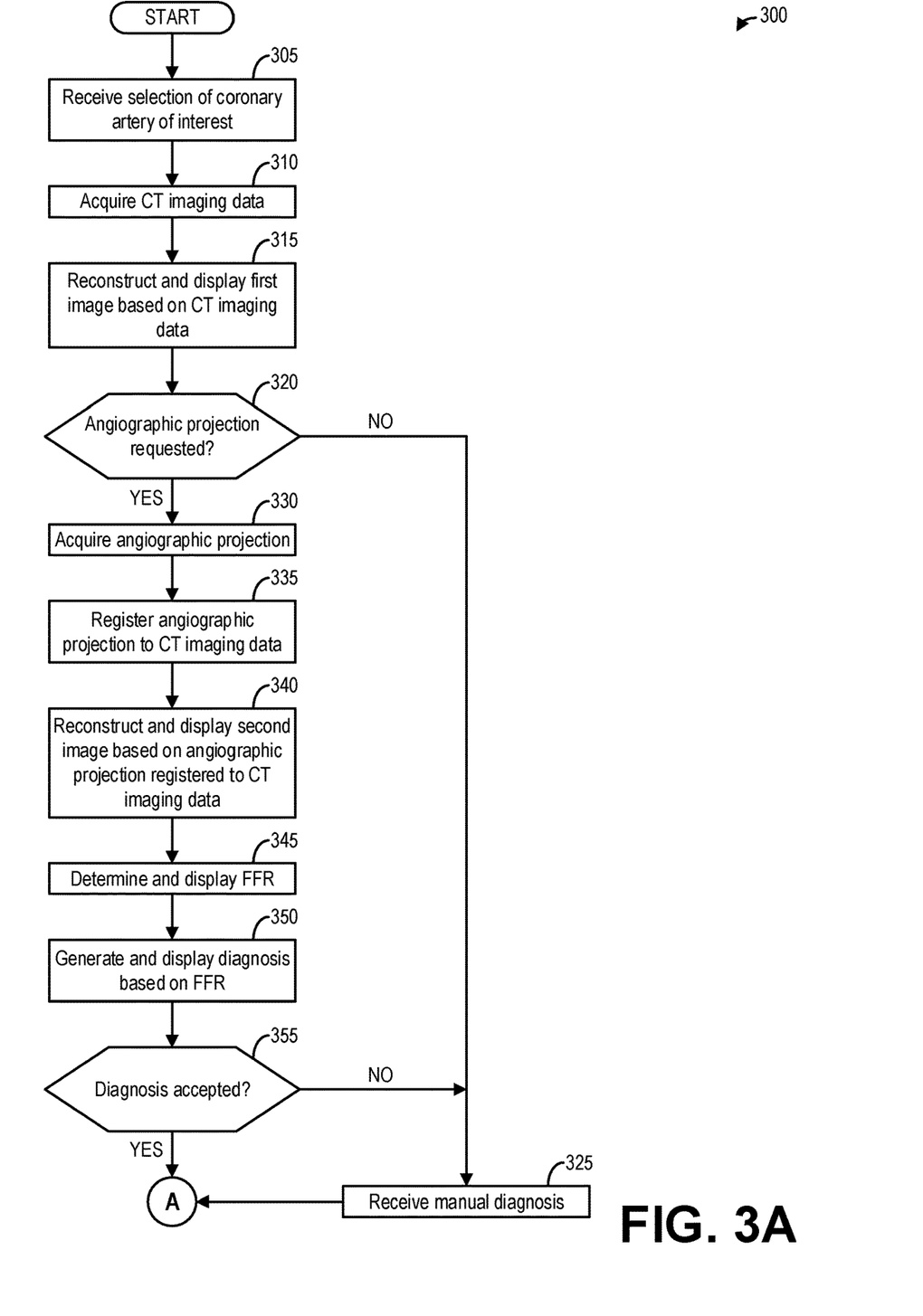
FIGS. 3A and 3B shows a flow chart of a method for automatically registering an angiographic projection to computed tomographic imaging data and determining a fractional flow reserve therefrom, according to an embodiment.
Figure 3B:
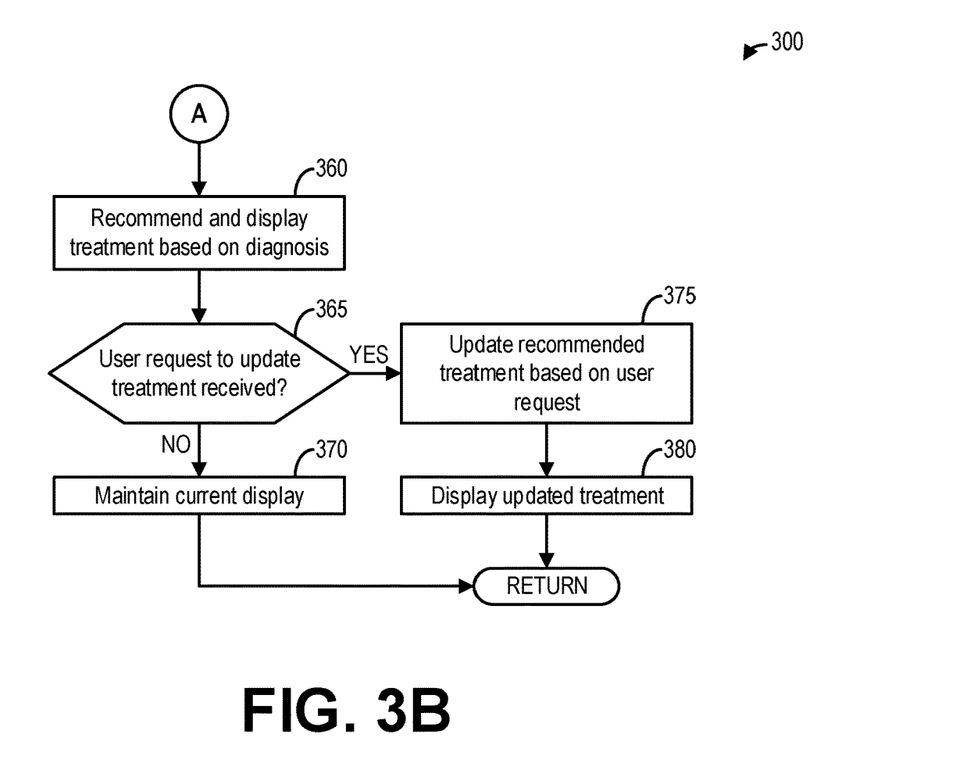

Referring now to FIGS. 3A and 3B, a flow chart is depicted, showing a method 300 for automatically registering an angiographic projection to CT imaging data and determining a FFR therefrom. Specifically, the angiographic projection may depict a coronary artery of interest, which may be correlated with a coronary tree as segmented from the CT imaging data. The FFR may then be determined based on the coronary artery of interest correlated to the coronary tree. Accordingly, a diagnosis may be generated and a treatment may be recommended therefor, which may be displayed to a user of a medical imaging system. It will be appreciated that, along with the diagnosis and the recommended treatment, various other information (e.g., the FFR, reconstructed images, etc.) may be displayed to the user at a display device of the medical imaging system. Accordingly, and as described in detail below with reference to FIG. 5, the user may interact with the display device via a user interface so as to add, remove, or alter displayed information. Though such displayed information is described with reference to specific steps of method 300, it will further be appreciated that each of the diagnosis, the recommended treatment, the FFR, the reconstructed images, etc. may be displayed at any time following generation or receipt of the given information.

Method 300 is described below with regard to the systems and components depicted in FIGS. 1 and 2. For example, in some embodiments, method 300 may be implemented on the imaging system 200 of FIG. 2. However, it will be appreciated that method 300 may be implemented with other systems and components without departing from the scope of the present disclosure. In some embodiments, method 300 may be implemented as executable instructions in any of the medical imaging systems described above with reference to FIGS. 1 and 2. In one embodiment, method 300 may be implemented in non-transitory memory of a computing device, such as the computing device 216 of the imaging system 200 in FIG. 2. It will further be appreciated that individual steps discussed with reference to method 300 may be added, removed, substituted, or interchanged within the scope of the present disclosure.

Method 300 may begin at 305 of FIG. 3A, where method 300 may include receiving a selection of one or more coronary arteries of interest of a patient. For example, the selection may be a user selection received at a user interface (e.g., 234) of a medical imaging system (e.g., 200), e.g., from a medical professional. Specifically, a given coronary artery of interest may be identified as contributing to coronary artery disease in the patient. For example, the given coronary artery of interest may have a stenosis (e.g., a region of calcification) or a coronary lesion. As an additional contributing factor, the patient may have a heart rate (e.g., a resting heart rate) higher than a threshold heart rate (e.g., 90 bpm). In some embodiments, the selection may comprise a single coronary artery of interest. In other embodiments, the selection may comprise a plurality of coronary arteries of interest.

At 310, method 300 may include acquiring CT imaging data. In some embodiments, the CT imaging data may be acquired as x-ray radiation attenuated by the patient. Specifically, in CT imaging, a contrast dye may be provided to the patient in a "non-invasive" manner (e.g., via intravenous injection). The contrast dye may be selected so as to absorb more X-ray photons than a surrounding tissue, arterial lumen, etc. As such, a contrast between X-rays attenuated by the dyed coronary arteries and surroundings thereof may be exacerbated. The attenuated X-rays may be acquired via the x-ray detector array (e.g., 108) disposed on a gantry (e.g., 102) of the medical imaging system (e.g., 200), which may be processed and received by the computing device (e.g., 216) as 3D CT imaging data. In some embodiments, the 3D CT imaging data may depict at least a portion of a coronary tree corresponding to the one or more coronary arteries of interest, or an entirety of the coronary tree.

In other embodiments, the CT imaging data may be acquired from an imaging library stored on a storage device of the medical imaging system (e.g., 200). In some embodiments, the imaging library may include CT imaging data depicting the coronary tree of the patient (e.g., previously acquired in a separate imaging session). In additional or alternative embodiments, the imaging library may include CT imaging data depicting coronary trees of a plurality of previous patients, where each of the plurality of previous patients may further be associated with patient information including one or more of patient age, patient weight, patient heart rate, patient blood pressure (e.g., systolic and diastolic), and patient medical history. The computing device (e.g., 216) may receive the patient information for the plurality of previous patients from the imaging library. Accordingly, for the patient having the one or more coronary arteries of interest, patient information including one or more of patient age, patient weight, patient heart rate, patient blood pressure (e.g., systolic and diastolic), and patient medical history may further be received and matched to patient information for a particular previous patient. The CT imaging data for the particular previous patient may then be received from the imaging library, wherein the CT imaging data may depict a coronary tree of the particular previous patient. It will be appreciated that, though the coronary tree depicted by the CT imaging data of the particular previous patient may be an approximation to the coronary tree of the patient, an accuracy of the approximation may be increased by utilizing a larger and more diverse library. By acquiring the CT imaging data from the imaging library, the patient having the one or more coronary arteries of interest may be subjected to fewer imaging procedures, thereby improving an overall patient experience.

At 315, method 300 may include reconstructing and displaying a first image based on the CT imaging data. In some embodiments, an image reconstructor (e.g., 230) may be employed to reconstruct the CT imaging data (e.g., via an analytic or iterative approach) into a viewable image (e.g., the first image). The first image may then be displayed to the user at a display device (e.g., 232) of the medical imaging system (e.g., 200). Accordingly, the user may manipulate the first image (e.g., alter a magnification thereof, move within the first image, obtain alternate views, etc.) via a user interface (e.g., 234) including the display device.

At 320, method 300 may include determining whether one or more angiographic projections are requested. In some embodiments, the CT imaging data may be determined (e.g., by the computing device 216, the user, or a combination thereof) to be sufficient to determine a diagnosis. In such embodiments, the one or more angiographic projections may not be requested and method 300 may proceed to 325, where method 300 may include receiving a manual diagnosis. For example, the user may determine the manual diagnosis based on the first image displayed via the display device (e.g., 232). The user may provide the manual diagnosis to the imaging system (e.g., 200) by inputting the manual diagnosis via the user interface (e.g., 234).

In other embodiments, the CT imaging data may be determined (e.g., by the computing device 216, the user, or a combination thereof) to be insufficient to determine the diagnosis. As an example, the CT imaging data may be determined by the computing device to be insufficient to determine an FFR of each of the one or more coronary arteries of interest above a threshold confidence level. In such embodiments, the one or more angiographic projections may be requested and method 300 may proceed to 330, where method 300 may include acquiring the one or more angiographic projections. Specifically, the one or more angiographic projections may respectively depict the one or more coronary arteries of interest, the one or more coronary arteries of interest respectively having one or more coronary lesions. In some embodiments, the one or more angiographic projections may be acquired via invasive angiographic imaging. That is, a catheter may be sequentially inserted and threaded into each of the one or more coronary arteries of interest, via which the contrast dye may be injected. As described above at 310, the contrast dye may absorb more X-ray photons than a surrounding tissue, lumen, etc., and may therefore exacerbate a contrast between X-rays attenuated by dyed features of the patient and surroundings thereof. The attenuated X-rays may then be acquired via an x-ray detector array (e.g., 108) of the medical imaging system (e.g., 200), which may be processed and received at the computing device (e.g., 216) as an angiographic projection. Specifically, the angiographic projection may include a single 2D depiction of a given coronary artery of interest and coronary arteries adjacent thereto.

In some embodiments, a single angiographic projection may be acquired for each of the one or more coronary arteries of interest. As such, in embodiments including a single coronary artery of interest, only one angiographic projection may be acquired. As such, patient discomfort due to invasive angiographic imaging may be effectively minimized.

In other embodiments, a plurality of angiographic projections may be acquired for a given coronary artery of interest. In such embodiments, a single angiographic projection may be selected from the plurality of angiographic projections, wherein the single angiographic projection may have a least amount of vessel superimposition (e.g., due to another coronary artery overlapping the coronary artery of interest or due to foreshortening of the given coronary artery of interest) of the plurality of angiographic projections. Thus, the single angiographic projection may be selected as a highest resolution depiction of the coronary artery of interest of the plurality of angiographic projections.

At 335, method 300 may include automatically registering the one or more angiographic projections to the CT imaging data. Specifically, centerlines and/or vessel edges of each of the coronary arteries of the coronary tree (or portion thereof) depicted by the CT imaging data may be segmented. In embodiments wherein the centerlines are segmented in the CT imaging data, a length and a 3D shape of each of the centerlines may be determined, such that the centerlines may be plotted in a Cartesian coordinate system. Based on the length and a rotated projection of the 3D shape of each of the centerlines of the coronary tree, the one or more coronary arteries of interest may be correlated (e.g., registered) to a length and a rotated projection of a 3D shape of a centerline corresponding to a matching coronary artery in the coronary tree (e.g., via a least-squares fit). In some embodiments, each of the coronary arteries of the coronary tree may be uniquely identified and labeled (e.g., as "left circumflex artery," "right marginal artery," etc.) based on the length and 3D shape of the respective centerline. Based on such identification, the one or more coronary arteries of interest may then be registered to the one or more matching coronary arteries of the coronary tree. As such, each of the one or more angiographic projections may be registered to the CT imaging data based on the length and the 3D shape of each of the segmented centerlines.

In specific embodiments, the one or more angiographic projections may be paired with the CT imaging data via an iterative algorithm which maintains pairing coherence by preserving a topology of the coronary tree. The iterative algorithm may achieve such pairing coherence by not merely assuming correspondence between bifurcation points observed in the one or more angiographic projections and in the CT imaging data. Instead, the iterative algorithm primarily relies on matching the centerlines of the one or more coronary arteries of interest with the centerlines of the coronary tree while restricting for connectivity at the bifurcation points. In some embodiments, the iterative algorithm may further attach a spline to each centerline of the coronary tree, where control points of each spline may be optimized under a double constraint of minimizing a distance to a given angiographic projection depicting a corresponding coronary artery of interest and maintaining a constant length of the corresponding coronary artery of interest.

In general, acquiring multiple angiographic projections may provide increased accuracy of a given coronary artery of interest, as dynamic changes in cardiac motion may be relevant for accurate determination of certain functional physiological metrics. However, collecting multiple angiographic projections may increase an overall imaging time, complicate an overall workflow, and increase patient discomfort. As described herein, by acquiring 3D CT imaging data to use in combination with (2D) angiographic projections, an overall number of angiographic projections may be reduced. Specifically, the 3D CT imaging data may provide increased accuracy of a 3D structure of at least a portion of the coronary tree which, when registered to a given angiographic projection, may result in improved accuracy in determining functional physiological metrics (e.g., FFR) relative to utilizing the angiographic projection alone, thereby precluding use of multiple angiographic projections. As one example, the overall number of angiographic projections may be limited to an overall number of coronary arteries of interest.

As another example, in specific embodiments wherein a single coronary artery of interest is selected, a single angiographic projection depicting the coronary artery of interest may be sufficient for subsequent determination of functional measures of cardiac health (e.g., FFR). In such embodiments, no additional angiographic projections may be registered to the CT imaging data. Accordingly, when the single angiographic projection is registered to the CT imaging data, the CT imaging data may provide a 3D representation of the coronary artery of interest which, in alternative examples, would be provided by multiple angiographic projections.

Indeed, acquiring a single angiographic projection for a given coronary artery of interest instead of multiple angiographic projections therefor further precludes manual labelling of the coronary artery of interest typically employed to register multiple 2D angiographic projections with one another to obtain the 3D representation of the coronary artery of interest. That is, in some embodiments, no manual labelling or marking of any angiographic projection is employed.

At 340, method 300 may include reconstructing and displaying a second image of the coronary tree based on the one or more angiographic projections registered to the CT imaging data. Accordingly, the second image may include the one or more angiographic projections "spliced" into reconstructed 2D projections of the (3D) CT imaging data (as described in detail below with reference to FIG. 5). In some embodiments, the reconstructed second image may be an image viewable by the user of the medical imaging system (e.g., 200) upon display at the display device (e.g., 232). Accordingly, the user may manipulate the second image (e.g., alter a magnification thereof, move within the second image, obtain alternate views, etc.) via the user interface (e.g., 234) including the display device. In such embodiments, one or more visual indicators may be generated on the second image for each stenosis or coronary lesion in the one or more coronary arteries of interest. As such, the user may easily locate a particular stenosis or coronary lesion depicted by the second image.

At 345, method 300 may include determining and displaying the FFR of each of the one or more coronary arteries of interest based on the one or more angiographic projections registered to the CT imaging data. In some embodiments, the FFR of each of the one or more coronary arteries of interest may be estimated based on one or more of a length of a respective centerline and a three-dimensional shape of the respective centerline.

In specific embodiments wherein the vessel edges are segmented in the CT imaging data, a transverse cross-section of each of the coronary arteries of the depicted coronary tree (or portion thereof) may be determined based on a corresponding vessel edge. In such embodiments, once the one or more angiographic projections have been registered to the CT imaging data, the transverse cross-section of each of the one or more coronary arteries of interest may be determined, and the FFR of each of the one or more coronary arteries of interest may further be estimated based on the transverse cross-section thereof. It will be appreciated by those of at least ordinary skill in the art that, as used herein with reference to coronary arteries, "transverse" may refer to a cross-section of a given coronary artery in any plane normal to a directional path of blood flow through the given coronary artery.

In some embodiments, the FFR may be estimated based on a reduced order model (such as the reduced order model described in detail below with reference to FIG. 4). In such embodiments, the reduced order model may be formed based on the length of each of the centerlines of the coronary arteries of the coronary tree and a vessel diameter of each of the coronary arteries of interest (where each vessel diameter may be determined based on the transverse cross-section of the respective coronary artery of interest). Accordingly, each of the coronary arteries of interest may be modeled based on each of the one or more angiographic projections and the CT imaging data, and remaining coronary arteries in the coronary tree (or portion thereof) may be modeled based on the CT imaging data.

At 350, method 300 may include automatically generating and displaying a diagnosis based on the FFR. Specifically, a relatively low FFR may indicate a significant stenosis or coronary lesion in the coronary artery of interest. For example, if the FFR is less than a threshold FFR (e.g., 0.80), then the stenosis or coronary lesion may be diagnosed as significant. The diagnosis may then be displayed to the user at the display device (e.g., 232), where the user interface (e.g., 234) including the display device may be configured so as to enable the user to accept or reject the diagnosis (e.g., via a confirmation checkbox, a text entry field, etc.). In specific embodiments, the computing device (e.g., 216) may indicate to the user that the FFR of at least one of the one or more coronary arteries of interest has not been determined above the threshold confidence level. In such embodiments, the user may be prompted at the user interface to review the diagnosis. In some embodiments, the computing device may wait for confirmation from the user regardless of whether or not the FFR of each of the one or more coronary arteries of interest has been determined above the threshold confidence level. However, in other embodiments, the computing device may automatically confirm that the FFR of each of the one or more coronary arteries of interest has been determined above the threshold confidence level and may automatically accept the diagnosis.

At 355, method 300 may include determining whether the diagnosis is accepted. For example, the user may evaluate the diagnosis and may determine that the diagnosis is potentially incorrect. Accordingly, the user may indicate that the diagnosis is rejected, and method 300 may proceed to 325 to receive the manual diagnosis from the user. For example, the user may determine the manual diagnosis based on the second image displayed via the display device (e.g., 232). The user may provide the manual diagnosis to the imaging system (e.g., 200) by inputting the manual diagnosis via the user interface (e.g., 234).

However, the user or the computing device (e.g., 216) may instead indicate that the diagnosis is accepted, and method 300 may proceed to 360 of FIG. 3B, where method 300 may include automatically recommending and displaying a treatment based on the generated diagnosis. For example, if the stenosis or coronary lesion has been diagnosed as significant (e.g., the FFR is less than the threshold FFR), then automatically recommending the treatment may include determining placement of a stent in the coronary artery of interest or recommending coronary bypass. As another example, if the stenosis or coronary lesion has been diagnosed as less significant (e.g., the FFR is greater than the threshold FFR), then automatically recommending the treatment may include recommending administration of prescription medication. The recommended treatment may then be displayed to the user at the display device (e.g., 232).

At 365, method 300 may include determining whether a user request to update the recommended treatment has been received via the user interface (e.g., 234). For example, the user (e.g., a medical professional), may not agree with the recommended treatment, and may provide an updated treatment as an alternative. If the user request has not been received (or if a user request confirming the recommended treatment has been received), then method 300 may proceed to 370, where method 300 may include maintaining a current display at the display device (e.g., 232). Method 300 may then end.

If the user request has been received, then method 300 may proceed to 375, where method 300 may include updating the recommended treatment based on the user request. At 380, method 300 may include displaying the updated treatment at the display device (e.g., 232), e.g., over the recommended treatment as initially displayed. Method 300 may then end.

Figure 4:
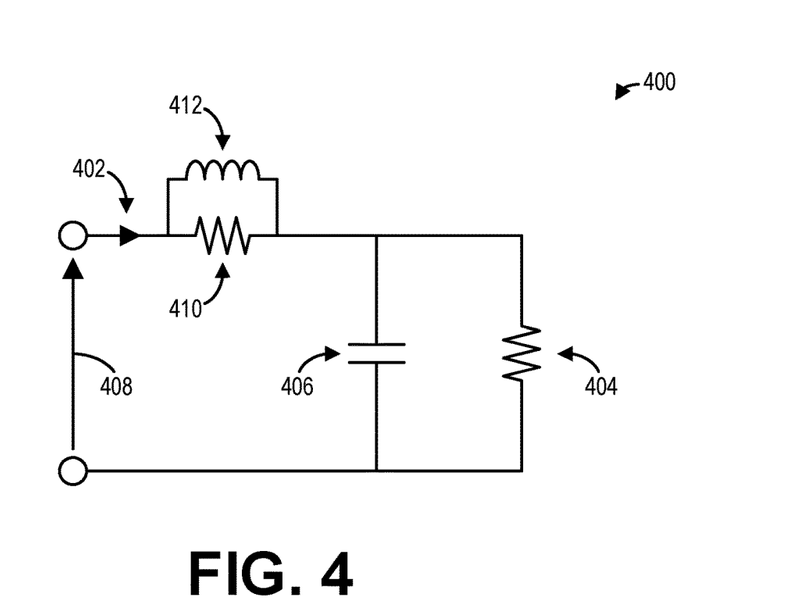
FIG. 4 shows a schematic diagram of an exemplary reduced order model of an exemplary portion of a coronary tree, according to an embodiment.
Figure 5:
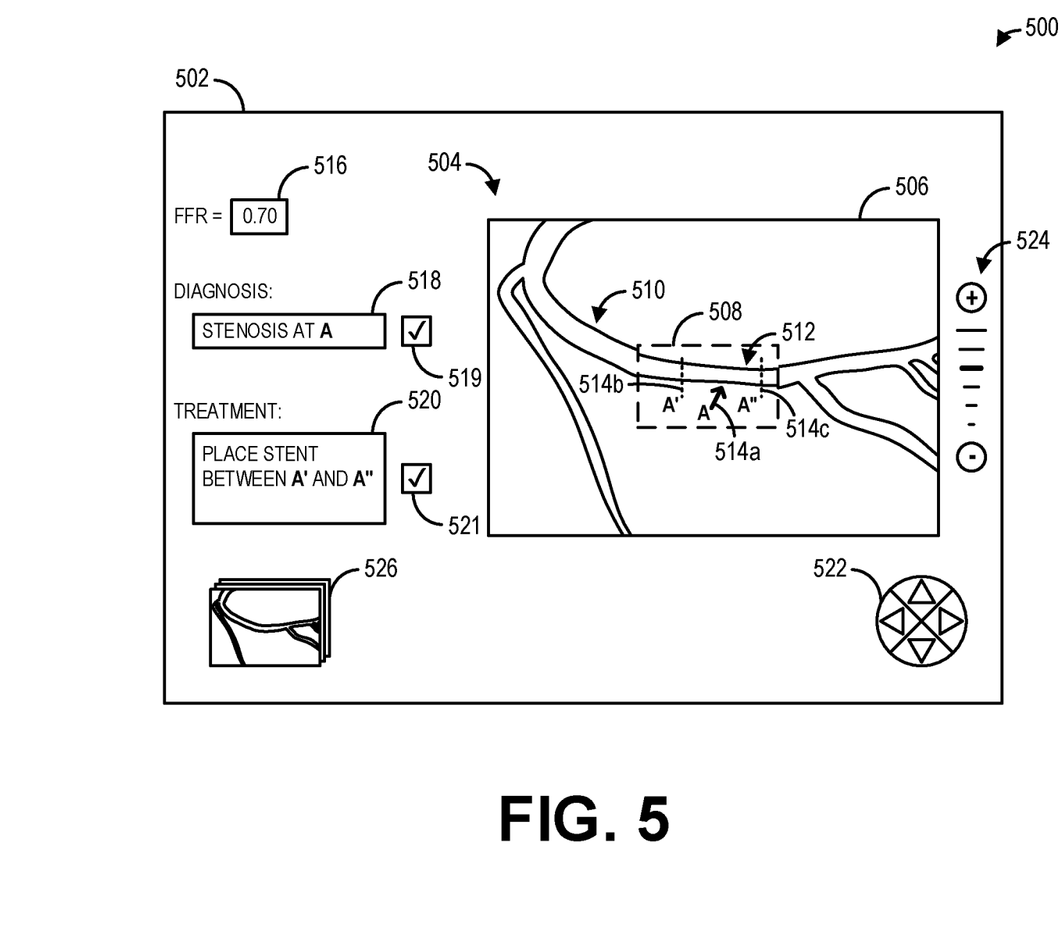
FIG. 5 shows an exemplary user interface display of a display device of the exemplary medical imaging system, according to an embodiment.

Referring now to FIG. 4, a schematic diagram 400 illustrating an exemplary reduced order model, or lumped parameter model, of an exemplary portion of a coronary tree is depicted. In one embodiment, the exemplary reduced order model may be employed to simulate blood flow and estimate a FFR of a coronary artery of interest depicted by a single angiographic projection in the exemplary portion of the coronary tree depicted by CT imaging data (such as at 345 of method 300, as described in detail above with reference to FIG. 3A).

As shown, the exemplary reduced order model may be depicted as a circuit diagram based on Windkessel physiology (referred to herein as a "Windkessel circuit"). As will be readily appreciated by those of at least ordinary skill in the art, Windkessel circuits may be defined by a number of diagrammatic elements representing respective physiological parameters. As such, though a four-element Windkessel circuit is depicted, it will be appreciated that Windkessel circuits having any number of elements may be considered within the scope of the present disclosure.

As shown in schematic diagram 400, a current 402 represents a volumetric inflow from pumping of the heart. A first resistor 404 may represent a total peripheral resistance, e.g., at a stenosis in the coronary artery of interest. Accordingly, the total peripheral resistance may be based upon a vessel length of the coronary artery of interest (e.g., a length of a centerline of the coronary artery of interest) and a vessel diameter of the coronary artery of interest at the stenosis. Further, a capacitor 406 may represent a total arterial compliance, and an electric potential 408 may represent an overall fluid pressure.

Each of the above diagrammatic elements may be present in a two-element Windkessel circuit. Accordingly, the two-element Windkessel circuit may be improved upon by adding a second resistor 410, which may represent resistance to blood flow due to a characteristic resistance of an aorta, and an inductor 412, which may represent an inertia of the blood flow. It will further be appreciated by those of at least ordinary skill in the art that the exemplary reduced order model of FIG. 4 may be expanded for multiple coronary arteries of interest, where a total peripheral resistance at each stenosis of each respective coronary artery of interest may be represented by an additional resistor.

Referring now to FIG. 5, an exemplary user interface display 500 of a display device 502 is depicted. In one embodiment, the display device 502 may be the display device 232 of the medical imaging system 200 shown in FIG. 2. The exemplary user interface display 500 may include a simultaneous display of a reconstructed image 504, a FFR 516, a diagnosis 518, and a recommended treatment 520.

As shown in the exemplary user interface display 500, the reconstructed image 504 may include an angiographic projection 508 "spliced" into CT imaging data 506. Specifically, the angiographic projection 508 may be registered to the CT imaging data by registering a coronary artery 510 depicted by the imaging data to a coronary artery of interest 512 depicted by the angiographic projection 508. In some embodiments, the reconstructed image 504 may be selectable via a user of the medical imaging system (e.g., via touch, a mouse, a keyboard, etc.) for further user manipulation. In a specific embodiment, a view of a portion of the reconstructed image 504 may be displayed instead of an entirety of the reconstructed image 504. As such, the user may be able to move the view of the reconstructed image 504. As one example, a user actuatable icon 522 may be operable to move the view of the reconstructed image 504 up, down, left, and right. As another example, a magnification bar 524 may be operable to increase or decrease a magnification of the reconstructed image 504. As yet another example, a directory 526 may provide further views or reconstructed images selectable for display.

As shown, the coronary artery of interest 512 may have a stenosis. The stenosis may be labeled with one or more visual indicators 514a, 514b, 514c. In some embodiments, as illustrated by the visual indicator 514a, the stenosis may be indicated by a directional arrow labeled with an alphanumeric character or string of characters (e.g., "A"). In additional or alternative embodiments, as illustrated by the visual indicators 514b and 514c, the stenosis may be indicated by a proximal dashed line (e.g., the visual indicator 514b) and a distal dashed line (e.g., the visual indicator 514c), wherein the proximal and distal dashed lines may be parallel to respective transverse planes of the coronary artery of interest 512, and wherein each of the proximal and distal dashed lines may be labeled with an alphanumeric character or string or characters (e.g., "A'," "A").

Each of the FFR 516, the diagnosis 518, and the recommended treatment 520 may be a text box editable by the user. In such embodiments, when the user selects a given text box for editing and alters text contained within the text box (e.g., if the user updates the recommended treatment 520), a background color of the text box may be altered relative to the rest of the exemplary user interface display 500 or a thickness of an outer edge of the text box may be increased. Further, checkboxes 519 and 521 may be displayed proximal to the diagnosis 518 and the recommended treatment 520, respectively. Accordingly, the user may select the checkbox 519 to accept or reject the diagnosis 518 (e.g., by filling the checkbox 519 with a checkmark or an X, respectively). Similarly, the user may select the checkbox 521 to accept or reject the recommended treatment (e.g., by filling the checkbox 521 with a checkmark or an X, respectively).

In this way, a single two-dimensional (2D) projection of a region of a coronary tree obtained via invasive angiographic techniques may be automatically registered to three-dimensional (3D) computed tomographic (CT) imaging data. Specifically, the single 2D projection may be selected to image a particular coronary artery with high resolution. A technical effect of automatically registering the single 2D projection to the 3D CT imaging data is that lower resolution regions in the 3D CT imaging data may be complemented by the single 2D projection, thereby increasing an accuracy of a calculated fractional flow reserve of the particular coronary artery and ultimately of diagnoses of coronary ailments. Further, via such automatic registration, a consistency of diagnosis, treatment, and health outcomes may be increased, concomitantly improving an overall patient experience. Additionally, by not acquiring multiple 2D projections, patient discomfort ascribed to the invasive angiographic techniques may be mitigated.

In one embodiment, a method for imaging a coronary artery of interest in a patient comprises acquiring computed tomography (CT) imaging data depicting a coronary tree, acquiring a single angiographic projection of the coronary artery of interest, registering the single angiographic projection to the CT imaging data, and determining a fractional flow reserve (FFR) of the coronary artery of interest based on the single angiographic projection registered to the CT imaging data. In a first example of the method, the coronary artery of interest has a stenosis, or the patient has a heart rate above a threshold heart rate. In a second example of the method, optionally including the first example of the method, acquiring the single angiographic projection is responsive to determining the CT imaging data insufficient to determine the FFR above a threshold confidence level. In a third example of the method, optionally including one or more of the first and second examples of the method, acquiring the CT imaging data depicting the coronary tree comprises receiving, for the patient, patient information comprising one or more of patient age, patient weight, patient heart rate, patient blood pressure, and patient medical history, matching the patient to a previous patient based on the patient information; and receiving, from an imaging library, the CT imaging data depicting the coronary tree, wherein the coronary tree is a coronary tree of the previous patient. In a fourth example of the method, optionally including one or more of the first through third examples of the method, the method further comprises, responsive to the FFR being less than a threshold FFR, automatically determining placement of a stent in the coronary artery of interest. In a fifth example of the method, optionally including one or more of the first through fourth examples of the method, registering the single angiographic projection to the CT imaging data comprises segmenting centerlines of the coronary tree depicted by the CT imaging data, determining a length and a three-dimensional shape of each of the centerlines, and registering the single angiographic projection to the CT imaging data based on the length and three-dimensional shape of each of the centerlines. In a sixth example of the method, optionally including one or more of the first through fifth examples of the method, determining the FFR of the coronary artery of interest based on the single angiographic projection registered to the CT imaging data comprises determining a transverse cross-section of the coronary artery of interest based on the single angiographic projection registered to the CT imaging data, and estimating the FFR for the coronary artery of interest based on one or more of the transverse cross-section, the length of a corresponding centerline, and the three-dimensional shape of the corresponding centerline. In a seventh example of the method, optionally including one or more of the first through sixth examples of the method, acquiring the single angiographic projection comprises selecting the single angiographic projection from a plurality of angiographic projections, the single angiographic projection having a least amount of vessel superimposition of the plurality of angiographic projections.

In another embodiment, a computing system comprises an x-ray imaging subsystem configured to acquire x-ray radiation, a user interface comprising a display device, a processor communicably coupled to each of the user interface and the x-ray imaging subsystem, and memory communicably coupled to the processor, the memory storing processor-executable instructions that cause the processor to receive, from the x-ray imaging subsystem, a single two-dimensional (2D) angiographic projection depicting a coronary artery of a coronary tree and a three-dimensional (3D) computed tomographic (CT) imaging data depicting the coronary tree, register the single 2D angiographic projection to the 3D CT imaging data, determine a fractional flow reserve (FFR) of the coronary artery based on the single 2D angiographic projection registered to the 3D CT imaging data, generate a diagnosis of the coronary artery based on the FFR, and display, on the display device, the diagnosis and the FFR. In a first example of the computing system, the memory stores further processor-executable instructions that cause the processor to automatically recommend a treatment for the coronary artery based on the diagnosis, and display, on the display device, the recommended treatment with the diagnosis and the FFR. In a second example of the computing system, optionally including the first example of the computing system, the memory stores further processor-executable instructions that cause the processor to receive, via the user interface, a user request to update the recommended treatment, and update the recommended treatment based on the user request. In a third example of the computing system, optionally including one or more of the first and second examples of the computing system, registering the single 2D angiographic projection to the 3D CT imaging data comprises segmenting centerlines of the coronary tree depicted by the 3D CT imaging data, determining a length and a 3D shape of each of the centerlines, and registering the single 2D angiographic projection to the 3D CT imaging data based on the length and the 3D shape of each of the centerlines. In a fourth example of the computing system, optionally including one or more of the first through third examples of the computing system, determining the FFR of the coronary artery based on the single 2D angiographic projection registered to the 3D CT imaging data comprises determining a vessel diameter of the coronary artery based on the single 2D angiographic projection registered to the 3D CT imaging data, and estimating the FFR for the coronary artery based on the vessel diameter and the length of a corresponding centerline. In a fifth example of the computing system, optionally including one or more of the first through fourth examples of the computing system, estimating the FFR for the coronary artery based on the vessel diameter and the length of the corresponding centerline comprises forming a reduced order model based on the length of each of the centerlines and the vessel diameter of the coronary artery, and estimating the FFR based on the reduced order model. In a sixth example of the computing system, optionally including one or more of the first through fifth examples of the computing system, in the reduced order model, the coronary artery is modeled based on each of the single 2D angiographic projection and the 3D CT imaging data and remaining coronary arteries in the coronary tree are modeled based on the 3D CT imaging data.

In yet another embodiment, a system for imaging one or more coronary lesions of a subject comprises an x-ray source, an x-ray detector array configured to detect x-ray radiation emitted by the x-ray source and attenuated by the subject, and a controller configured with instructions in non-transitory memory that when executed cause the controller to acquire computed tomographic (CT) imaging data of the subject, register the one or more angiographic projections to the CT imaging data, acquire one or more angiographic projections respectively depicting one or more coronary arteries, the one or more coronary arteries respectively having the one or more coronary lesions, and reconstruct an image of a coronary tree of the subject based on the one or more angiographic projections registered to the CT imaging data. In a first example of the system, the instructions are further executable to generate a visual indicator on the reconstructed image for each of the one or more coronary lesions. In a second example of the system, optionally including the first example of the system, the system further comprises a display device, and the instructions are further executable to display, via the display device, the reconstructed image with the visual indicator for each of the one or more coronary lesions. In a third example of the system, optionally including one or more of the first and second examples of the system, the instructions are further executable to determine a fractional flow reserve for each of the one or more coronary arteries based on the one or more angiographic projections registered to the CT imaging data. In a fourth example of the system, optionally including one or more of the first through third examples of the system, the CT imaging data depicts a coronary tree comprising the one or more coronary arteries, and registering the one or more angiographic projections to the CT imaging data comprises segmenting centerlines of the coronary tree depicted by the CT imaging data, and registering each of the one or more coronary arteries to the centerlines of the coronary tree.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for imaging a coronary artery of a coronary tree having multiple coronary arteries in a patient, the method comprising:
   first, acquiring computed tomography (CT) imaging data depicting the coronary tree;
   after acquiring the CT imaging data and in response to requesting one or more angiographic projections, acquiring a single angiographic projection of the coronary artery, wherein acquiring the single angiographic projection comprises selecting the single angiographic projection from a plurality of angiographic projections, the single angiographic projection having a least amount of vessel superimposition of the plurality of angiographic projections;
   registering the single angiographic projection to the CT imaging data, wherein registering the single angiographic projection to the CT imaging data comprises:
      segmenting centerlines of the coronary tree depicted by the CT imaging data;
      determining a length of the centerlines and a three-dimensional shape of the centerlines; and registering the single angiographic projection to the CT imaging data based on the length of the centerlines and the three-dimensional shape of each of the centerlines; and determining a fractional flow reserve (FFR) of the coronary artery from the single angiographic projection registered to the CT imaging data.

2. The method of claim 1, wherein the coronary artery of interest has a stenosis, or
wherein the patient has a heart rate above a threshold heart rate.

3. The method of claim 1, wherein acquiring the CT imaging data depicting the coronary tree comprises:
receiving, for the patient, patient information comprising one or more of patient age, patient weight, patient heart rate, patient blood pressure, and patient medical history;
matching the patient to a previous patient based on the patient information; and
receiving, from an imaging library, the CT imaging data depicting the coronary tree, wherein the coronary tree is a coronary tree of the previous patient and is an approximation of a coronary tree of the patient.

4. The method of claim 1, further comprising, responsive to the FFR being less than a threshold FFR, automatically determining placement of a stent in the coronary artery of interest.

5. The method of claim 1, wherein determining the FFR of the coronary artery of interest based on the single angiographic projection registered to the CT imaging data comprises:
determining a transverse cross-section of the coronary artery of interest based on the single angiographic projection registered to the CT imaging data; and
estimating the FFR for the coronary artery of interest based on one or more of the transverse cross-section, the length of a corresponding centerline, and the three-dimensional shape of the corresponding centerline.

6. A computing system, comprising:
an x-ray imaging subsystem configured to acquire x-ray radiation;
a user interface comprising a display device;
a processor communicably coupled to each of the user interface and the x-ray imaging subsystem; and
memory communicably coupled to the processor, the memory storing processor-executable instructions that cause the processor to:
receive, from the x-ray imaging subsystem, a single two-dimensional (2D) angiographic projection depicting a coronary artery of a coronary tree having multiple coronary arteries and a three-dimensional (3D) computed tomographic (CT) imaging data depicting the coronary tree, wherein the single 2D angiographic projection is selected from a plurality of angiographic projections, the single 2D angiographic projection having a least amount of vessel superimposition of the plurality of angiographic projections;
register the single 2D angiographic projection to the 3D CT imaging data by segmenting centerlines of the coronary tree depicted by the 3D CT imaging data, determining a length of the centerlines and a three-dimensional shape of the centerlines, and registering the single 2D angiographic projection to the 3D CT imaging data based on the length of the centerlines and the three-dimensional shape of each of the centerlines;

determine a fractional flow reserve (FFR) of the coronary artery from the single 2D angiographic projection registered to the 3D CT imaging data;
generate a diagnosis of the coronary artery based on the FFR; and
display, on the display device, the diagnosis and the FFR.

7. The computing system of claim 6, wherein the memory stores further processor-executable instructions that cause the processor to:
automatically recommend a treatment for the coronary artery based on the diagnosis; and
display, on the display device, the recommended treatment with the diagnosis and the FFR.

8. The computing system of claim 7, wherein the memory stores further processor-executable instructions that cause the processor to:
receive, via the user interface, a user request to update the recommended treatment; and
update the recommended treatment based on the user request.

9. The computing system of claim 6, wherein determining the FFR of the coronary artery based on the single 2D angiographic projection registered to the 3D CT imaging data comprises:
determining a vessel diameter of the coronary artery based on the single 2D angiographic projection registered to the 3D CT imaging data; and
estimating the FFR for the coronary artery based on the vessel diameter and the length of a corresponding centerline.

10. The computing system of claim 9, wherein estimating the FFR for the coronary artery based on the vessel diameter and the length of the corresponding centerline comprises:
forming a reduced order model based on the length of each of the centerlines and the vessel diameter of the coronary artery; and
estimating the FFR based on the reduced order model.

11. The computing system of claim 10, wherein, in the reduced order model, the coronary artery is modeled based on each of the single 2D angiographic projection and the 3D CT imaging data and remaining coronary arteries in the coronary tree are modeled based on the 3D CT imaging data.

12. A system for imaging one or more coronary lesions of a subject, the system comprising:
an x-ray source;
an x-ray detector array configured to detect x-ray radiation emitted by the x-ray source and attenuated by the subject; and
a controller configured with instructions m non-transitory memory that when executed cause the controller to:
first, acquire computed tomographic (CT) imaging data depicting a coronary tree comprising one or more coronary arteries of the subject;
after the CT imaging data of the subject is acquired, determine if an angiographic projection is requested;
in response to determining that the angiographic projection is not requested, receive a manual diagnosis; and
in response to a request for one or more angiographic projections, acquire a single angiographic projection depicting a coronary artery of the coronary tree having multiple coronary arteries, the coronary artery having the one or more coronary lesions, by selecting the single angiographic projection from a plurality of angiographic projections, the single angiographic projection having a least amount of vessel superimposition of the plurality of angiographic projections;

register the one or more angiographic projections to the CT imaging data by segmenting centerlines of the coronary tree depicted by the CT imaging data, determining a length of the centerlines and a three-dimensional shape of the centerlines, and registering each of the one or more coronary arteries to the centerlines of the coronary tree based on the length of the centerlines and the three-dimensional shape of each of the centerlines; and reconstruct an image of the coronary tree of the subject from the one or more angiographic projections registered to the CT imaging data.

13. The system of claim 12, wherein the instructions are further executable to generate a visual indicator on the reconstructed image for each of the one or more coronary lesions.

14. The system of claim 13, further comprising a display device, and wherein the instructions are further executable to display, via the display device, the reconstructed image with the visual indicator for each of the one or more coronary lesions.

15. The system of claim 12, wherein the instructions are further executable to determine a fractional flow reserve for each of the one or more coronary arteries based on the one or more angiographic projections registered to the CT imaging data.

16. The computing system of claim 6, wherein the memory stores further processor-executable instructions that cause the processor to:

determine whether the diagnosis is accepted;

responsive to a determination that the diagnosis is not accepted, receive a manual diagnosis from a user; and responsive to a determination that the diagnosis is accepted, display a treatment based on the diagnosis.

* * * * *